United States Patent [19]
Stone

[11] Patent Number: 5,964,752
[45] Date of Patent: Oct. 12, 1999

[54] ARTICULAR CARTILAGE SURFACE SHAPING APPARATUS AND METHOD

[76] Inventor: Kevin R. Stone, 1 Throckmorton La., Mill Valley, Calif. 94941

[21] Appl. No.: 09/017,352

[22] Filed: Feb. 2, 1998

[51] Int. Cl.⁶ .................................................. A61B 17/39
[52] U.S. Cl. .............................................. 606/27; 607/98
[58] Field of Search .......................... 606/27, 28; 607/96, 607/98, 99

[56] References Cited

U.S. PATENT DOCUMENTS

| | | | |
|---|---|---|---|
| 5,348,554 | 9/1994 | Imran et al. | 606/41 |
| 5,542,928 | 8/1996 | Evans et al. | 604/113 |
| 5,620,440 | 4/1997 | Heckele et al. | 606/28 |
| 5,704,934 | 1/1998 | Neuwirth et al. | 606/28 |
| 5,880,432 | 9/1998 | Swanson | 606/49 |

*Primary Examiner*—Michael Peffley
*Assistant Examiner*—Roy D. Gibson
*Attorney, Agent, or Firm*—Lappin & Kusmer LLP

[57] ABSTRACT

The invention disclosed is a method and apparatus for imparting a desired shape to a surface-to-be-shaped of articular cartilage in the joint of a mammal. The method discloses applying steam to a surface-to-be-shaped to soften the cartilage at and near that surface and positioning a form defining the desired shape adjacent to that softened region. A bias pressure is applied to impart the desired shape and the form is removed. An apparatus for practicing the method includes an element for generating and delivering steam to the surface-to-be-shaped to soften the surface and includes a form for molding the softened surface.

14 Claims, 3 Drawing Sheets

ARTICULAR CARTILAGE SURFACE SHAPING APPARATUS AND METHOD

The present invention relates to the field of surgical methods and instruments for treatment of certain articular cartilage defects in the joint of a mammal, and more particularly, for imparting a desired shape to the surface of articular cartilage.

BACKGROUND OF THE INVENTION

Irregular surfaces on articular cartilage in the joints of mammals are considered defects known to compromise the function of such joints. When possible, arthroscopic surgery is the preferred method for remediating such defects. Presently, there exist several arthroscopic devices for the treatment of such articular cartilage defects. These devices can generally be divided into three categories. The first category includes bipolar heating devices such as a bipolar wand produced, for example, by Arthrocare. The second category includes laser devices. The third category includes radio frequency devices produced, for example, by Mitek and Oratec.

All of these prior art devices effect the application of heat to the surface-to-be-treated, in response to which the collagen fiber bundles that make up articular cartilage at or near the surface "melt", or soften, and become moldable. Articular cartilage that has been melted or softened by application of heat is referenced to hereinafter as "softened". The depth of the penetration of heat, however, has a negative effect on the cartilage consequences. It is preferred that the heat penetration is minimized in order to prevent damage to the underlying bone. In fact, laser devices have been virtually abandoned for treatment of articular cartilage defects because the laser energy often penetrates the bone, sometimes resulting in osteonecrosis. Invariably, all the prior art devices have the additional drawback of having tips with elevated temperatures, which often burn the surrounding tissue. This burning can leave a charred residue in the joint which can later cause complications in the joint after the surgery. Thus, a need remains for a device and method for treating articular cartilage defects which would have relatively little heat penetration and would not burn the surrounding tissue in the mammalian joint.

SUMMARY OF THE INVENTION

The present invention provides a surgical technique in which articular cartilage can be repaired without damaging the surrounding tissue or the underlying bone. In one embodiment, the invention provides a method for imparting a desired contour to the surface articular cartilage in a joint, for example smoothing a rough surface of the cartilage. The method may be performed arthroscopically or in an open joint. The method comprises a first step of applying steam to the surface-to-be-treated, resulting at least partial melting i.e., "softening" of collagen fiber bundles at and near that surface. A form is provided having an applicator surface that has a contour which defines the desired contour to be imparted to the surface-to-be-shaped. The applicator surface is positioned opposite the surface-to-be-shaped and following the softening step and, pressure is applied to bias that applicator against the surface-to-be-shaped. Preferably, the contour of the applicator surface is smooth so that the form smooths the softened surface. The form is removed. Upon cooling of the cartilage, the surface maintains the shape of the form.

The invention includes an apparatus that may be used to effect the above described surgical technique. The apparatus preferably includes a elongated element having a proximal end and a distal end. The elongated element is preferably cylindrical and has dimensions suitable for use in arthroscopic procedures.

The elongated element defines an internal void region at the distal end. A conduit for fluid extends from the proximal end of the elongated element into the void region. An applicator element at the distal end of the elongated element spans the void region, thereby closing the void region within the elongated element. In various forms of the invention, the applicator element has a smooth shaped exterior applicator surface which can be used to form or mold a "melted" cartilage region to a desired shape. For example, the exterior surface may be shaped as planar, cylindrical concave, cylindrical convex, ellipsoidal concave, ellipsoidal convex, spherical concave, and spherical convex.

In preferred forms of the invention, the void region is thermally coupled to a heating element. Liquid is directed through the conduit into the void region. In or near that void region, the liquid is exposed to heat from the heating element and the liquid is changed to gas phase. Preferably, the liquid is water, which is vaporized into steam. Other fluids may be used. The applicator element has a plurality of passages extending therethrough which allow the steam to pass from the void region through the applicator tip to the exterior of the elongated element. In use, the perforated applicator element is positioned adjacent to the surface-to-be-shaped of the articular cartilage. The steam from the elongated element melts or softens collagen fiber bundles at and near the surface of the cartilage. Then the applicator tip is pressed against the melted or softened cartilage, causing the cartilage to conform to the shaped of the exterior surface of the tip, for example smoothing the heretofore rough surface.

BRIEF DESCRIPTION OF THE DRAWINGS

For a more complete understanding of the nature and the objects of the invention, reference should be made to the following detailed description and the accompanying drawings in which like reference numerals refer to like elements and in which.

DESCRIPTION OF THE PREFERRED EMBODIMENT

Articular cartilage defects in the joints of any mammal may be repaired in accordance with the invention. Preferably, articular cartilage defects in the joints of humans are repaired using the method and apparatus of the invention. The invention is suitable for use in many joints, preferably arthroscopically, but alternatively in a surgically opened joint. Preferably, the method of the invention is used to smooth articular cartilage surfaces in the hip. More preferably, the method of the invention is used to smooth articular cartilage surfaces in the ankle. Most preferably, the method of the invention is used to smooth articular cartilage surfaces in the knee.

By way of example, after a rough surface of articular cartilage is identified during routine arthroscopic surgery, the method of the invention maybe performed on a knee as follows. The method is preferably performed with the articular cartilage apparatus of the invention.

The rough surface-to-be-smoothed is first located within the knee joint. Steam is applied to the defect. The heat from the steam melts or softens the collagen fiber bundles in the cartilage. Once the collagen bundles melt or soften, the cartilage is moldable. While the cartilage remains soft, pressure is applied via a shaped form to substantially smooth a rough area of the cartilage defect. As the heat from the steam dissipates, the cartilage cools and the collagen bundles solidify. When the shaped form is removed, the surface of the surface of the cartilage remains in the substantially smoothed state.

Figure 1:
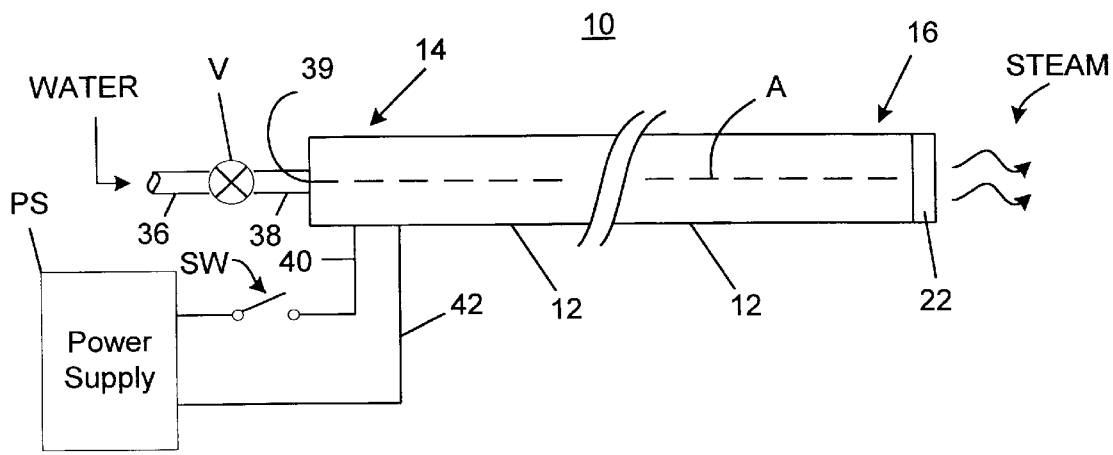
FIG. 1 shows, partially in schematic form and partially in plan view, an articular cartilage shaping apparatus of the invention.
Figure 2:
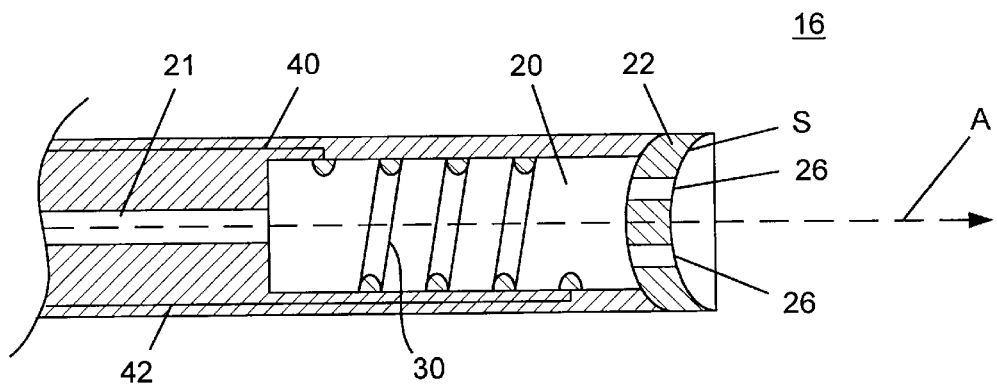
FIG. 2 shows, in section, the distal tip of the apparatus of FIG. 1.
Figure 3:
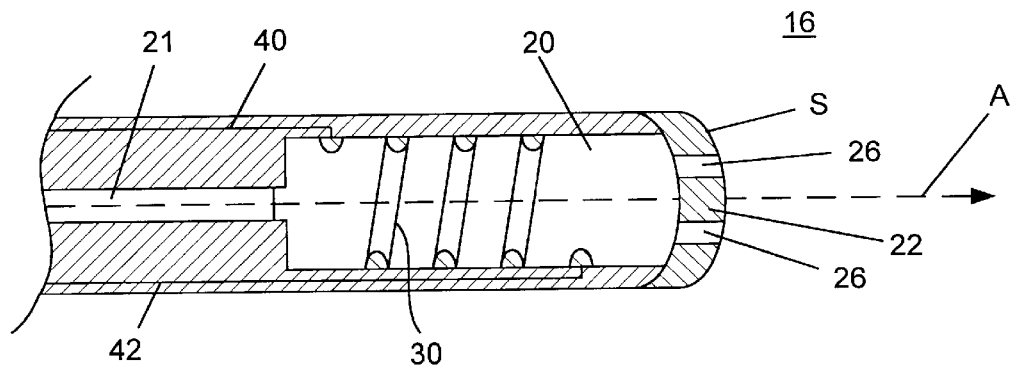
FIGS. 3–8 show, in section, distal tips of alternate embodiments of the articular cartilage shaping apparatus of the invention.
Figure 4:
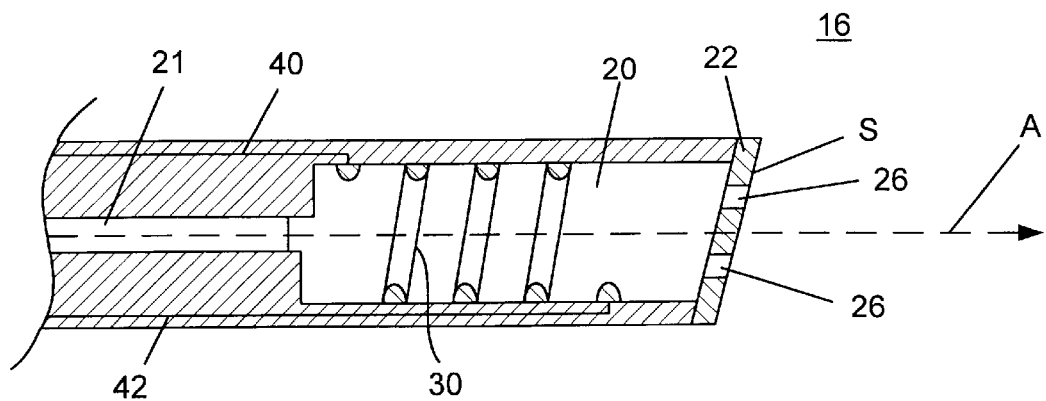
Figure 5:
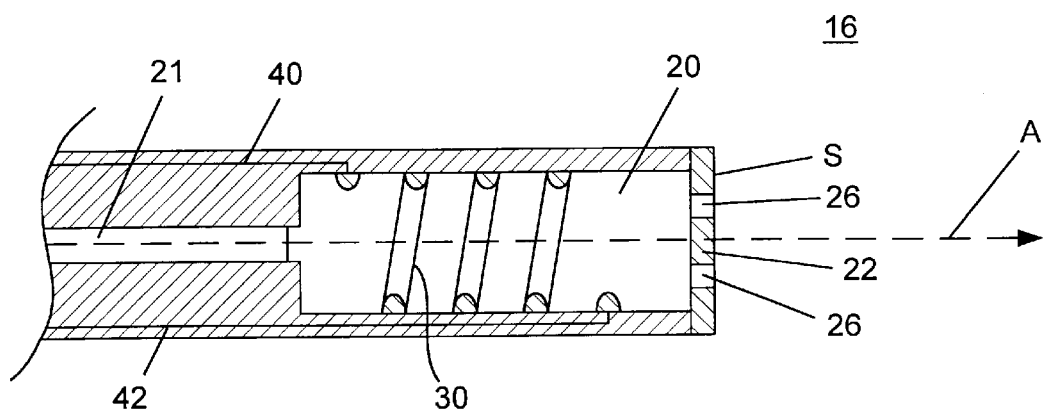
Figure 6:
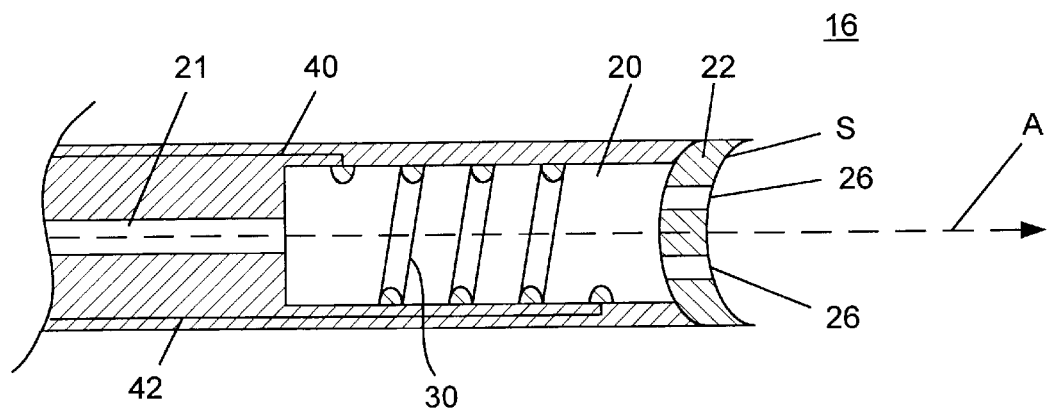
Figure 7:
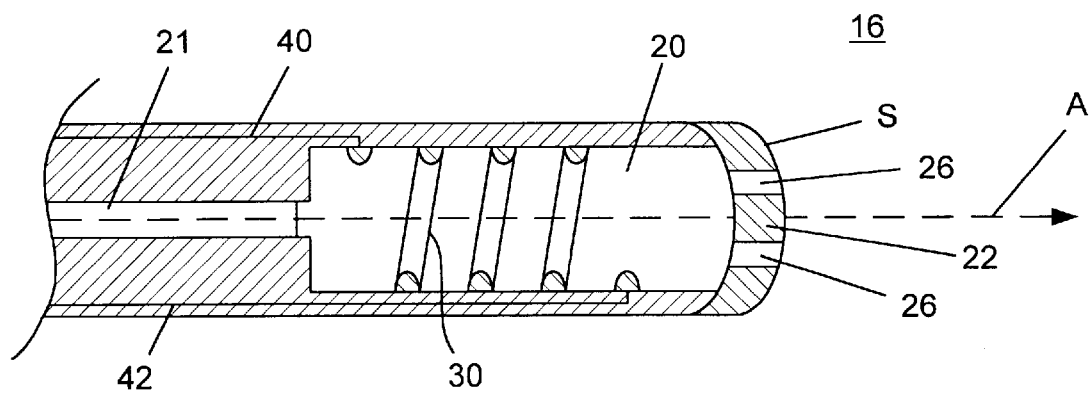

The method of the invention is preferably performed using the articular cartilage surface shaping system 10 illustrated in FIGS. 1 and 2. The system 10 includes an elongated wand element 12 extending along a central axis A. The wand element 12 has a proximal end 14 and a distal end 16. The wand element 12 has cylindrical interior void region 20 near the distal end 16. A fluid channel 21 extends along axis A between the proximal end 14 and the void region 20. An applicator element 22, spans the void region 20 and thereby encloses the void region 20 within the distal end 16 of the wand element 12. The applicator element 22 contains one or more (two in the illustrated embodiment) passages 26, which allow fluid communication between the void region 20 and the exterior to the wand element 12. The exterior surface S of the applicator 22 is spherical or ellipsoidal concave.

In the illustrated embodiment, a resistive heating element 30 is disposed within the void region 20. The heating element 30 is helical in shape and is affixed to the sidewall defining void region 20. A power supply PS is coupled in series with a switch SW and conductor 40 and 42 across heating element 30. In operation, the distal end 16 is placed so that the surface S of applicator element 22 is adjacent to a cartilage surface-to-be-shaped. Then, a voltage is selectively applied (in response to operation of switch SW) across the heating element 30. In response to the applied voltage, the heating element 30 heats the void region 20. A fluid pump (not shown) delivers water via valve V and tubes 36 and 38 to a water inlet 39 of the system. The water travels through the fluid conduit 21 and into the void region 20. The water is then exposed to heat from the heating element 30 and the water is vaporized into steam. The steam escapes from the void region 20 through the passages 26 of the applicator element 22. FIG. 2 shows an applicator element 22 with convex exterior surface S.

In response to that escaping steam, the collagen fiber bundles at and near the cartilage surface soften. Following opening of switch SW, the distal tip 16 cools, and may be pressed against the surface-to-be-smoothed so that the surface S of the applicator element 22 can impart a smooth surface to the cartilage.

FIGS. 3 through 8 illustrate alternative forms for applicator element 22. The surface S may be spherical convex or ellipsoidal convex (FIG. 3), planar at an oblique transverse angle with respect to axis A (FIG. 4) planar perpendicular to axis A (FIG.5), cylindrical concave (FIG. 6), cylindrical convex (FIG. 7), or any other desired shape, smooth or rough. These various forms for surface S allow the system of the invention to be used in different regions of various affected joints as necessary.

Figure 8:
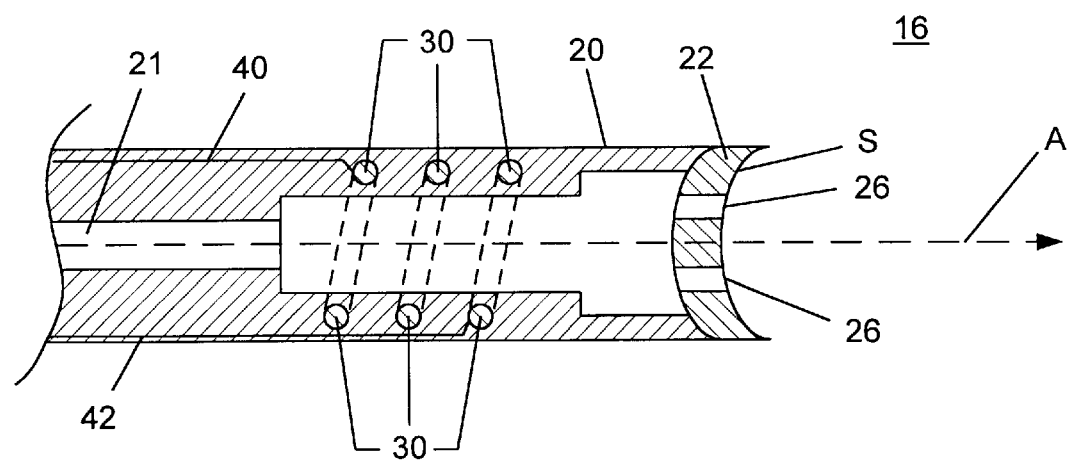

In another form of the invention, the heating element 30 may be disposed fully within the cavity 20, i.e. apart from the sidewall, and in yet another form, that element 30 may be embedded within the material forming wand element 12 as shown in FIG. 8.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An apparatus for imparting a desired shape to a surface-to-be-shaped of articular cartilage in a joint of a mammal, comprising:

A. an elongated wand element extending along a central axis between a proximal end and a distal end, said element defining an interior void region extending from said distal end;

B. a fluid conduit extending through said wand element from said proximal end to points within said void region;

C. a selectively operable heating element thermally coupled to said void region, whereby said fluid is vaporizable in said void region; and D. an applicator element at said distal end and extending transverse to said central axis and spanning said void region and having an exterior surface adjacent to an exterior region, said applicator element including one or more passages extending therethrough from said void region to said exterior region, said exterior surface having a contour substantially corresponding to said desired shape.

2. An apparatus according to claim 1 further comprising a fluid pump and associated means for driving a fluid through said conduit from said proximal end to said void region.

3. An apparatus according to claim 1 wherein said exterior surface of said applicator element is substantially planar.

4. An apparatus according to claim 3 wherein said substantially planar surface is substantially perpendicular to said central axis.

5. An apparatus according to claim 3 wherein said substantially planar surface is at an oblique angle relative to said central axis.

6. An apparatus according to claim 1 wherein said exterior surface of said applicator element is cylindrical convex.

7. An apparatus according to claim 1 wherein said exterior surface of said applicator element is cylindrical concave.

8. An apparatus according to claim 1 wherein said exterior surface of said applicator element is ellipsoidal convex.

9. An apparatus according to claim 1 wherein said exterior surface of said applicator element is ellipsoidal concave.

10. An apparatus according to claim 1 wherein said exterior surface of said applicator element is spherical convex.

11. An apparatus according to claim 1 wherein said exterior surface of said applicator element is spherical concave.

12. An apparatus according to claim 1 wherein said heating element includes a resistance element.

13. An apparatus according to claim 1 wherein said heating element is disposed within said void region.

14. An apparatus according to claim 1 wherein said heating element is disposed within the wand element and adjacent to said void region.

* * * * *